United States Patent [19]
Matsuyama et al.

[11] Patent Number: 5,888,804
[45] Date of Patent: Mar. 30, 1999

[54] PROCESSES FOR PRODUCTION OF OPTICALLY ACTIVE QUINUCLIDINOL

[75] Inventors: Akinobu Matsuyama, Tsukuba; Takeshi Hamatani, Arai, both of Japan

[73] Assignee: Daicel Chemical Industries, Ltd., Osaka, Japan

[21] Appl. No.: 34,284

[22] Filed: Mar. 4, 1998

[30] Foreign Application Priority Data

Mar. 4, 1997 [JP] Japan ................................. 9-048928

[51] Int. Cl.$^6$ .................................................. C07C 00/00
[52] U.S. Cl. ............................ 435/280; 435/830; 435/874
[58] Field of Search ..................................... 435/280, 830, 435/874

[56] References Cited

U.S. PATENT DOCUMENTS 5,215,918  6/1993  Muchmore .............................. 435/280

Primary Examiner—David A. Redding
Attorney, Agent, or Firm—Birch, Stewart, Kolasch & Birch, LLP

[57] ABSTRACT

The present invention provide processes for producing an optically active quinuclidinol from a quinuclidinone using an asymmetric reduction by a microorganism and enzyme with commercial advantages in simple and easy manner. In the present invention, permit a microorganism or preparation thereof to act on a quinuclidinone (3-quinuclidinone), and recover or harvest an optically active quinuclidinol produced (3-quinuclidinol). The microorganisms capable of producing an (R)-3-quinuclidinol from a 3-quinuclidinone include the genus Nakazawaea, the genus Candida and the genus Proteus. The microorganisms capable of producing an (S)-3-quinuclidinol from a 3-quinuclidinone include the genus Arthrobacter, the genus Pseudomonas and the genus Rhodosporidium.

6 Claims, No Drawings

PROCESSES FOR PRODUCTION OF OPTICALLY ACTIVE QUINUCLIDINOL

FIELD OF THE INVENTION

The present invention relates to a process for producing an optically active quinuclidinol (e.g. 3-quinuclidinol) from a quinuclidinone (e.g. 3-quinuclidinone) with the use of a microorganism.

BACKGROUND OF THE INVENTION

An optically active quinuclidinol (e.g. 3-quinuclidinol) is an important intermediate for physiologically active or pharmacologically active components (such as medicines). For the production of an optically active 3-quinuclidinol, there are known processes such as a process which comprises acylating and optically resolving a racemic modification as a starting material with a subtilisin protease (U.S. Pat. No. 5,215,918 A), a process which comprises reducing the starting material imine, which is prepared from a 3-quinuclidinone and an optically active phenethylamine, with the use of a sodium borohydrate (Synth. Commun. (1992), 22(13), 1895–911), a process which comprises hydrolyzing an acetylated racemic modification after resolving with a tartaric acid (Acta Pharm. Suec. (1979), 16(4), 281–3) and a process which comprises optically resolving a racemic form of butyl ester as a starting material with the use of an esterase of horse blood serum (Life Sci. (1977), 21 (9), 1293–302).

These methods, however, have difficulty in producing an optically active quinuclidinol (e.g. 3-quinuclidinol) with commercial advantages in simple and easy manner. Moreover, the efficient production of an optically active quinuclidinol using asymmetric reduction by a microorganism and enzyme has never been reported.

SUMMARY OF THE INVENTION

Accordingly, an object of the present invention is to provide a process for producing an optically active quinuclidinol (especially 3-quinuclidinol) with commercial advantages in a simple and easy manner.

Another object of the present invention is to provide a novel process capable of producing an optically active quinuclidinol (especially 3-quinuclidinol) efficiently using an asymmetric reduction by a microorganism and enzyme.

The present inventors were interested in a process for producing an optically active quinuclidinol from a quinuclidinone with the aid of a microorganism or preparation thereof in order to obtain an optically active quinuclidinol with an economically advantageous, easy and simple manner. After extensive researches, they found that an optically active quinuclidinol (e.g. 3-quinuclidinol) can efficiently be produced from a quinuclidinone (e.g. 3-quinuclidinone) by using an asymmetric reduction caused by a microorganism or its enzyme. The present invention has been accomplished on the basis of the above findings.

Namely, the present invention provides a process for producing an optically active quinuclidinol which comprises:

permitting a microorganism or preparation thereof to act on a quinuclidinone (e.g. 3-quinuclidinone), and recovering or harvesting the produced optically active quinuclidinol (e.g. 3-quinuclidinol). The micro-organisms employed in this process may be any strain of microorganism capable of producing an (R)-quinuclidinol from a quinuclidinone (e.g. the genus Nakazawaea, the genus Candida, the genus Proteus and the like) and of microorganism capable of producing an (S)-quinuclidinol from a quinuclidinone (e.g. the genus Arthrobacter, the genus Pseudomonas, the genus Rhodosporidium and the like).

DETAILED DESCRIPTION OF THE INVENTION

Quinuclidinones as a substrate include a ketone of quinuclidine (compound containing the carbonyl group at 2-position or 3-position) such as 2-quinuclidinone, 3-quinuclidinone and the like. In the present invention, a microorganism and a preparation thereof having asymmetric reduction capability are allowed to act on such substrate so as to produce a corresponding optically active quinuclidinol (e.g. 2-quinuclidinol, 3-quinuclidinol and the like). In the preferred embodiment, an optically active 3-quinuclidinol can efficiently be produced from a 3-quinuclidinone.

The microorganisms in the present invention may be, as far as having the asymmetric reduction capability, any strain of microorganism. For example, the microorganisms that belong to any of the genus Nakazawaea, the genus Candida and the genus Proteus can be exemplified as microorganisms having the capability of producing an (R)-quinuclidinol (especially (R)-3-quinuclidinol) by acting on a quinuclidinone (especially 3-quinuclidinone).

The examples of microorganisms for producing an (R)-quinuclidinol from a quinuclidinone are listed below:

The genus Nakazawaea: *Nakazawaea holstii* IFO 0980, etc.,

The genus Candida: *Candida magnoliae* DSM 70638, etc.,

The genus Proteus: *Proteus vulgaris* IFO 3167, etc.

Moreover, as microorganisms capable of producing an (S)-quinuclidinol (especially (S)-3-quinuclidinol) by acting on a quinuclidinone (especially 3-quinuclidinone), there may be exemplified the microorganisms which belong to, for example, the genus Arthrobacter, the genus Pseudomonas, the genus Rhodosporidium and the like.

The examples of microorganisms for producing an (S)-quinuclidinol from a quinuclidinone are listed below:

The genus Arthrobacter: *Arthrobacter ureafaciens* IFO 12140 etc.,

The genus Pseudomonas: *Pseudomonas sp.* ATCC 21025 etc.,

The genus Rhodosporidium: *Rhodosporidium diobovatum* IFO 0688 etc.

As apparent from the above, the present invention discloses, as microorganisms having capability of producing an optically active quinuclidinol from a quinuclidinone, at least one strain of microorganisms selected from the group consisting of the genus Nakazawaea, the genus Candida, the genus Proteus, the genus Arthrobacter, the genus Pseudomonas and the genus Rhodosporidium.

Any of the wild strains, mutants and recombinant strains, which can be obtained by a genetic engineering technique such as cell fusion or gene recombination, and the like can advantageously be employed.

The microorganisms identified by IFO numbers are listed in "LIST OF CULTURES MICROORGANISMS 10th EDITION 1996" published by Institute for Fermentation. Osaka (IFO) and are available from the same institute. The microorganisms designated by DSM numbers are listed in "CATALOGUE OF STRAIN 1989" published by Deutsche Sammlung von Mikroorganismen (DSM) and are available from the DSM. The microorganisms identified by ATCC numbers are listed in "CATALOGUE OF BACTERIA AND PHAGES Eighteenth edition 1992" published by American Type Culture Collection (ATCC) and are available from the ATCC.

The medium for growing microorganisms for use in the present invention is not restricted as far as the selected strain may grow and multiply therein. The medium normally includes, for example, carbon sources (saccharides such as glucose, fructose, sucrose, etc.; alcohols such as ethanol, glycerol, etc.; organic acids such as fumaric acid, acetic acid, propionic acid, etc.; hydrocarbons such as paraffin etc.; other carbon sources; and various mixtures thereof) and nitrogen sources (inorganic acid ammonium salts such as ammonium sulfate, ammonium phosphate, etc.; organic acid ammonium salts such as ammonium citrate, etc.; inorganic or organic nitrogen-containing compounds such as yeast extract, meat extract, malt extract, peptone, polypeptone, urea, etc.). In the medium, there may be incorporated appropriate amounts of those nutrients which are commonly employed in the cultivation of microorganisms, such as inorganic salts, trace metal salts and vitamins. Where necessary, to the medium may be added factors which promote multiplication of a microorganism, factors which improve its ability to produce the object compound of the invention, compounds for maintaining a given pH of the medium (such as buffer substances), etc. A microorganism may be habituated or acclimated by a quinuclidinone.

The cultivation of the microorganism may be carried out under conditions optimal for the growth and multiplication of the microorganisms, for example, at a pH in the range of about 3.0 to 9.5 (preferably about 4 to 8) and a temperature in the range of about 20° to 45° C. (preferably about 25° to 35° C.). The cultivation may be performed aerobically or anaerobically for one to five days.

Any technique for reducing quinuclidinone asymmetrically may be employed as far as the microorganisms or the preparation thereof is allowed to act on a quinuclidinone. The techniques of asymmetric reduction may be, for example, (1) a technique which comprises mixing or blending a quinuclidinone with a culture broth as it is to conduct the reaction, (2) a technique which comprises separating the microbial cells from the culture broth, e.g. by centrifugation, resuspending the cells, either as they are or after washing, in a buffer solution, water or the like, and adding a quinuclidinone to the resultant cell suspension to conduct the reaction, (3) a technique which comprises using not viable cells but a treated preparation of cells (such as disrupted cells, acetone-treated preparations, lyophilized preparations, enzymes obtained from the cells, etc.), (4) a technique which comprises using the cells or preparations thereof by fixing on carriers (e.g. polyacrylamide gel). In many cases, a higher yield of the object compound may be obtained by adding a carbon source such as glucose, sucrose, ethanol and methanol which serves as an energy source. The quinuclidinone may be used as it is, or in the form of a solution in which an organic solvent will not interfere with the reaction or a dispersion prepared with a surfactant, and may be added in a lump at the beginning of the reaction or in several installments.

The reaction conditions can be selected from the ranges that will not lower the activation of microorganisms or preparations thereof, for example, at a pH of about 3 to 9 (preferably 4 to 8), a temperature of about 10° to 60° C. (preferably 20° to 40° C.). The reaction can be conducted with stirring for about 1 to 120 hours. The optimal cell concentration and quinuclidinone concentration are not particularly restricted as far as the production efficiency of the desired optically active compound will not adversely affected. The cell concentration may be, for example, about 1 to 300 g/L on a dry cell basis. The concentration of a quinuclidinone (substrate) is preferably, for example, about 0.1 to 10% by weight.

The optically active quinuclidinol produced by the reaction can be recovered or harvested by conventional procedures. For example, the optically active compound can be obtained by subjecting the reaction mixture, after separation of the cells where necessary, to the separation and purification means or steps (such as extraction with an organic solvent, crystallization, recrystallization, column chromatography, concentration and distillation). The separation and purification means may be used by itself or as combination thereof. Any of the organic solvents (alcohols such as butanol; hydrocarbons such as hexane, cyclohexane, toluene; halogenated hydrocarbons such as chloroform, methylene chloride; esters such as ethyl acetate; ketones; ethers and mixtures thereof) may be employed.

According to the present invention with the aid of a microorganism or preparation thereof, an optically active quinuclidinol (especially 3-quinuclidinol) can be produced from a quinuclidinone with commercial advantages in a simple and easy manner. Furthermore, an optically active quinuclidinol (especially 3-quinuclidinol) can efficiently be produced by using an asymmetric reduction caused by microorganism or enzymes.

EXAMPLE

The following example is intended to show the invention in further detail and should by no means be construed as delimiting the scope of the invention.

The quantitative determination of 3-quinuclidinone and 3-quinuclidinol in the reaction mixture was carried out by subjecting the mixture to gas chromatography [column; column 3% silicon OV-17/uniport HP (80/100 mesh) 3.2 cm$\phi$×2.1 m; column temperature; 100° C., detection; FID, detection temperature; 250° C., injection temperature; 200° C.].

The optical purity determination was carried out by subjecting the optically active 3-quinuclidinol extracted from the reaction mixture to a benzoylation reaction with a benzoyl chloride, and subjecting the resultant to high performance liquid chromatography using an optical resolution column [column; Chiralpack AD (0.46 cm$\phi$×25 cm); moving phase; hexane/ethanol/diethylamine=95/5/0.1, column temperature; 20° C., wavelength detected; 254 nm, flow rate: 1.0 ml/min.]. An optically active (R)-compound (optical rotation: minus) was detected by retaining for 12 min., and an optically active (S)-compound (optical rotation: plus) was detected by retaining for 23 minutes.

Example 1

[Cell-preparing media]

Cell-preparing medium for a yeast

Glucose 2.0 weight %

Yeast extract 0.3 weight %

Malt extract 0.3 weight %

Polypeptone 0.5 weight % pH 6.0

Cell-preparing medium for a bacterium

Glucose 2.0 weight %

Yeast extract 0.3 weight %

Meat extract 0.3 weight %

Polypeptone 0.5 weight %

Ammonium sulfate 0.2 weight %

Potassium dihydrogen-phosphate 0.1 weight %

Magnesium sulfate 0.05 weight % pH 7.0

A Sakaguchi's flask was charged with 25 ml of the cell-preparing medium described above. After sterilizing the flask at a temperature of 121° C. for 15 minutes, the flask was inoculated with one of the microorganisms shown in Table 1. The inoculated flask was incubated under shaking at 30° C. for one day. Subsequently, cells were isolated by centrifuging to obtain viable cells.

After that, a test tube of inner diameter of 21 mmφ was charged with a mixture of 2 ml which contains glucose of 2% by weight, calcium carbonate of 2% by weight and quinuclidinone of 0.5% by weight, and the viable cells prepared above, and the reaction was conducted on a reciprocating shaker at 30° C. for three days.

After completion of the reaction, a pH of the supernatant separated by centrifuge was adjusted to a pH of 12, and then, the supernatant was diluted appropriately. The quinuclidinol produced was determined by gas chromatography. The supernatant of which pH was adjusted was dehydrated by rotary evaporator, and a quinuclidinol was extracted with 2 ml of butanol. After separating from the solvent, the quinuclidinol was dissolved in methylene chloride, and was subjected to benzoylation with benzoyl chloride by the conventional process. The resultant compound was analyzed by high performance liquid chromatography, and its optical purity was measured.

The results will be shown in Table 1.

TABLE 1

| Name of the Strain | quinuclidinol (mg/ml) | Optical Purity (% ee) | Absolute Configuration |
|---|---|---|---|
| *Nakazawaea holstii* IFO 0980 | 1.3 | 92 | R |
| *Candida magnoliae* DSM 70638 | 2.5 | 49 | R |
| *Proteus vulgaris* IFO 3167 | 3.7 | 80 | R |
| *Arthrobacter ureafaciens* IFO 12140 | 1.2 | 95 | S |
| Pseudomonas sp. ATCC 21025 | 1.5 | 76 | S |
| *Rhodosporidium diobovatum* IFO 0688 | 1.6 | 4 | S |

What is claimed is:

1. A process for producing an optically active quinuclidinol which comprises:

permitting a microorganism or a preparation thereof to act on a quinuclidinone; and recovering or harvesting the product optically active quinuclidinol.

2. A process for producing an optically active quinuclidinol according to claim 1, which comprises:

permitting a microorganism or a preparation thereof to act on a 3-quinuclidinone to produce an optically active 3-quinuclidinol.

3. A process for producing an optically active quinuclidinol according to claim 2, wherein said microorganism is at least one strain selected from the group consisting of the genus Nakazawaea, the genus Candida, the genus Proteus, and capable of producing an (R)-3-quinuclidinol from a 3-quinuclidinone.

4. A process for producing an optically active quinuclidinol according to claim 3, wherein said microorganism is at least one strain selected from the group consisting of *Nakazawaea holstii, Candida magnoliae, Proteus vulgaris*.

5. A process of producing an optically active quinuclidinol according to claim 2, wherein said microorganism is at least one strain selected from the group consisting of the genus Arthrobacter, the genus Pseudomonas and the genus Rhodosporidium, and capable of producing an (S)-3-quinuclidinol from a 3-quinuclidinone.

6. A process for producing an optically active quinuclidinol according to claim 5, wherein said microorganism is at least one strain selected from the group consisting of *Arthrobacter ureafaciens*, Pseudomonas sp. and *Rhodosporidium diobovatum*.

* * * * *